United States Patent [19]

Holzner

[11] Patent Number: 4,990,381
[45] Date of Patent: Feb. 5, 1991

[54] MULTI-LAYER SANDWICH SHEET AND PACKAGING USING THE SAID SHEET

[75] Inventor: Günter Holzner, Grand-Lancy, Switzerland

[73] Assignee: Firmenich SA, Geneva, Switzerland

[21] Appl. No.: 220,711

[22] Filed: Jul. 18, 1988

[30] Foreign Application Priority Data

Jul. 22, 1987 [CH] Switzerland .................. 2781/87

[51] Int. Cl.⁵ .................. A61K 31/74; A61L 21/904
[52] U.S. Cl. ...................... 428/35.3; 239/34;
424/78; 428/339; 428/474.4; 428/457; 428/480;
428/522; 428/523; 428/905
[58] Field of Search ............ 428/905, 35.3, 474.4,
428/474.7, 475.2, 339, 522, 523, 457, 480;
239/55, 57, 34; 424/78, 83

[56] References Cited

U.S. PATENT DOCUMENTS

| | | | |
|---|---|---|---|
| 4,631,231 | 12/1986 | Stendel et al. | 428/905 |
| 4,634,614 | 1/1987 | Holzner | 428/905 |
| 4,720,409 | 1/1988 | Spector | 428/905 |
| 4,722,815 | 2/1988 | Shitanai | 428/905 |
| 4,808,454 | 2/1989 | Saitoh | 428/905 |

FOREIGN PATENT DOCUMENTS 0215480 4/1987 European Pat. Off. .

Primary Examiner—James Seidleck
Attorney, Agent, or Firm—Pennie & Edmonds

[57] ABSTRACT

Multi-layer laminated sandwich sheet, comprising at least two layers which are superimposed and stuck together by welding or gluing, one layer being constituted by a material impervious to the active volatile agents of a perfuming or deodorizing composition, of an aroma or of an insecticidal or bactericidal substance, and the other layer being composed of a film made from a polymer or a copolymer with a polyolefin base or from a copolymer of polyamide and polyether, which film contains, in dispersed and homogeneous phase, a base constituted by a perfuming or deodorizing composition, an aroma or an insecticidal or bactericidal substance, and packaging utilizing the said sheet.

20 Claims, 3 Drawing Sheets

MULTI-LAYER SANDWICH SHEET AND PACKAGING USING THE SAID SHEET

BRIEF SUMMARY OF THE INVENTION

The present invention relates to a multi-layer laminated sandwich sheeting, comprising at least two layers superimposed and stuck together by welding or gluing. One of these layers comprises a material impervious to the active volatile agents of a perfuming or deodorizing composition, of a flavouring agent (aroma) or of an insecticidal or bactericidal substance, and the other layer a film made from a polymer or a copolymer with a polyolefin base or from a copolymer of polyamide and polyether, this film being 10 to 300 microns thick and containing, in dispersed and homogeneous phase, a base constituted by a perfuming or deodorizing composition, an aroma or an insecticidal or bactericidal substance in a proportion of 0.1 to 50% by weight in relation to the weight of the polymeric base in which it is incorporated.

The present invention relates further to a process as described above, which process is characterized in that at least two polymeric materials are separately and simultaneously extruded in a current of air or of an inert, gas. One of these polymeric materials comprises a polyolefin resin base or is made from a copolymer of polyamide and polyether, being pre-mixed, in a homogeneous manner with an active base comprising a perfuming or deodorizing composition, a flavouring agent (aroma) or an insecticidal or bactericidal substance and the other constitut polymeric material being inpervious to the volatile agents of the said active base. The separate and simultaneous extrusions create base, and a multi-layer polymeric film, these layers being stuck together, and arranged, in such a way that the outer layer is constituted by the impervious polymeric material and the inner layer is constituted by the polymeric material containing the active base.

This invention provides also a packaging comprising a sandwich sheet as described above.

BACKGROUND OF THE INVENTION

The present invention relates to the sphere of packing and packaging. In particular, its subject is an industrial packing for products or materials which can give off volatile vapors or for those on which it is at least desired to confer an odor during the period before their consumption or activation, during which period the product is in closed packaging. It relates for example to cosmetic products, various perfumed products, air fresheners, detergents or fabric softeners, paper, textiles, insecticides, flavourings, foods or tobacco.

As will emerge in more detail in the remainder of this description, the packaging in the invention constitutes a medium capable of diffusing volatile or sanitizing vapours and is therefore generally intended to improve the consumer's perception of the packaged products or materials.

It is undisputed that the odorizing properties of a product often have a determining effect on the consumer. In many cases and for a certain category of products, they define, often unconsciously, the propensity to buy.

Manufacturers have applied themselves to increase this signal by trying to confer or intensify the odorizing characteristics of the products offered for consumption. However, there are obvious, practical limitations. It is actually difficult to increase the odourizing intensity of a product beyond certain limits without having a negative effect on the desired olfactory harmony. In other words, the odor of a product should be perceptible and agreeable and thus confer a distinctive character to the product, without however being overpowering.

Moreover, it is known that the consumer attaches importance to the first impression he receives of a product. The fragrance which is given off from a product which has just been unpacked can have a determining impression regarding acceptance of the product itself. Various solutions are known which consist in perfuming the packaging material and several processes have been suggested for this purpose.

There exists scented packaging materials in the commercial world, is generally consisting of paper, cardboard or plastic. Plastic has been the subject of particular attention. Due to the implementation of the so-called "master-batch" technique, concentrates of perfuming agent are prepared in matrices constituted by the same polymeric resin, generally a polyolefin resin, as that which is used for the preparation of the final product. Products, that products with a polyolefin matix, intended for the "master-batch" process and characterized by a high content of volatile perfuming substances, have recently appeared on the market. These are resins with a low-density polyethylene base (LPDE), of polypropylene and of copolymers of ethylene vinyl acetate (see for example: Polyiff (registered trade mark); origin: Int. Flavors and Fragrance, Inc.).

These polyolefin concentrates are generally prepared by incorporating the perfume in appropriate mixers at temperatures which vary according to the polymeric base. The polyethylene for example is treated at a temperature lying between 80° and 180° C., enabling a viscous mass to be obtained to which the desired perfume is added before cooling and granulation. Such a process meets with a major, practical difficulty, the incorporation of the perfume at a high temperature in fact causes olfactory losses and modifications to some of its constituents, this limiting the choice of suitable perfuming bases.

On the other hand, the perfuming of plastic sheeting also meets with major problems. In fact, the manufature of sheeting is essentially carried out by one of the following methods:
a. extrusion coating
b. sheet die extrusion
c. blown extrusion In each of these methods, the polymer is subject to a thermal treatment of shorter or longer duration, followed by compression through a nozzle of appropriate geometry. When this compression is accompanied by an injection of air or of an inert gas, and the nozzle has an annular shape, as is the case with blown extrusion, a product is obtained which is in the form of a cylinder whose walls are constituted by the plastic material now reduced to a thin layer of a homogeneous thickness. By cutting lengthways, unilayer or multilayer sheets are then obtained. Now, the perfuming of sheets by means of a perfume concentrate, in the form of master batch, is badly suited to the processes we have just described because in each of the variants mentioned, the perfume is subject to considerable temperature stresses, this causing a denaturation in a good many cases. Moreover, this phenomenon is still more pronounced in the blown extrusion process, where the combined action of the heat and of the current of hot air causes substantial evaporation of the volatile constituents of a purifying base, from the surface of the hot film which is directly exposed to the atmosphere.

PREFERRED EMBODIMENTS OF THE INVENTION

The present invention provides a solution to the problem put forward. The polymeric sheet resulting from the process of the invention has in fact the desired sanitizing or aromatizing characteristics and can be used as a plastic packaging material. The process of the invention does not require the use of special equipment, this being not the least of its advantages.

The subject of the present invention is more particularly a multi-layer laminated sandwich sheet, comprising at least two layers which are superimposed and stuck together by welding or gluing one of said layers is constituted by a material impervious to the active volatile agents of a perfuming or deodorizing composition, of a flavouring agent (aroma) or of an insecticidal or bactericidal substance and the other layer is composed of a carrying film made from a polyolefin-based polymer or a copolymer or from a polyamide and polyether copolymer, this film being 10 to 300 microns thick and containing, in dispersed and homogeneous phase, a base constituted by a perfuming or deodorizing composition, an aroma or an insecticidal or bactericidal substance in a proportion of 0.1 to 50% by weight in relation to the weight of the polymeric base in which it is incorporated.

As a polyolefin resin for the preparation of the carrying film for the active base, one can use polyethylene, polypropylene, copolymers of ethylene and propylene or copolymers of ethylene with vinyl acetate or ethyl acrylate. Surlyn (registered trade mark of Du Pont de Nemours) is perfect for this purpose. As a material impervious to the volatile agents, one can use a polyamide or polyester resin or a film of aluminum.

The sheet of the invention can be manufactured with the help of a blown extrusion process, which process is characterized by the simultaneous extrusion in a current of air or of inert gas, of at least two polymeric materials. One polymeric materials is having a polyolefin resin base or is a copolymer of polyamide and polyether and is mixed in a homogeneous manner, with an active base constituted by a perfuming or deodorizing composition, an aroma or an insecticidal or bactericidal substance, and the other polymeric material is impervious to the volatile agents of the said active base. The sheet being characterized in that the extrusion gives rise to a polymeric film with multiple layers which are stuck together and arranged in such a way that the outer layer is constituted by the impervious material and the inner layer is constituted by the polymeric material containing the active base.

As indicated above, blown extrusion takes place under the effect of a current of air. When active bases constituted by compositions susceptible to oxidation are used, such an extrusion can easily be carried out by the blowing of an inert gas. Nitrogen is perfect for this purpose.

In the present invention, "perfuming base" is understood to mean any perfuming substance or mixture of perfuming substances, both in the solitary state or in solution or suspension in their diluting agents, solvents or usual co-ingredients. These terms comprise in particular organic solutions which are generally non miscible in water and have an appreciable vapour pressure. Such perfuming bases can be constituted by compounds belonging to separated chemical classes and comprising for example esters, ethers, alcohols, aldehydes, ketones, acetals, nitriles, terpene hydrocarbons, nitrogenous or sulphurous heterocyclic compounds and essential natural oils. The particular choice of the perfuming base depends on the odourizing effect sought, on the nature of the product that one wishes to package, and of course on the taste and preferences of the creator of the scent.

Typical examples of useful perfuming compounds are given in the literature, and S. Arctander, Perfume and Flavor Chemicals, Montclair, N.J. (USA), (1969) can be quoted for this purpose.

"Deodorizing base" is understood to mean a substance capable of concealing the odour and of inhibiting the proliferation of bacteria, for example those responsible for the decomposition of sweat. A good many bactericidal and bacteriostatic products are known and used for this purpose. As an example one can quote hexachlorophene, dichlorophenol, trichlorosalicylanilide (Anobial), tribromosalicylanilide (TBS), tetrachlorosalicylanilide (TCSA) and trichlorocarbanilide (TCC).

As an aroma one can use one of the aromatizing compositions generally used to give, improve or modify the taste and the aroma of foods, drinks or tobacco. Should the case arise, one can of course use specific, isolated aromatic substances, such as the aromatic, natural essences or the pure, synthetic compounds. Among the effective volatile substances which can be used for this purpose, one should mention those described in the specialised works such as that of S. Arctander (work quoted above) and Fenaroli's Handbook of Flavor Ingredients, 2nd Edition, CRC Press, Cleveland, Ohio (1975).

As an insecticidal agent one can use extract of pyrethrum, DDVP (origin: Ciba-Geigy, Basel, Switzerland) and Vaporthrin (origin: Sumitomo, Osaka, Japan), As mentioned above, the manufacture of polymeric sheets according to the invention does not require special equipment; a normal apparatus for blown extrusion is sufficient and the detailed description of such a machine is superfluous here (see the specialized works; for example "Kunstsoffverarbeitung" by Schwarz et al., Vogel-Verlag, 2nd edition (1981), Wuerzburg (FRG).

The preliminary mixing of the polyolefin resin acting as a medium for the active, perfuming, bactericidal or other type of base, can also be carried out in an ordinary, simple apparatus. The active base can be premixed in a concentrated form in such a way as to constitute a master-batch which is added to the mass of the polymeric resin subjected to extrusion. By carrying out the operation with the help of two or even three different sorts of polymeric resin, one can operate in such a way that the resulting film is constituted by two, if applicable, three layers, stuck together and arranged so that the outer layer is constituted by an impervious material and the inner layer, and if applicable the intermediate layer, is constituted by the polymeric material containing the active base.

The result is that under the protective effect exerted by the impervious outer layer, the volatile constituents of the active base will be retained in the mass of the inner layer without notable evaporation, in spite of the entraining action exerted by the current of hot air. The resulting sheet will therefore be characterized by a uniform content of an active base of homogeneous composition and the dispersion of the latter will be practically eliminated during the whole extrusion and shaping operation. Used in the manufacture of packaging which are generally pliable and which are closed by means of welding or gluing, such a sheet has the outstanding advantage of enabling the active base to be preserved during the storage period and of keeping the said base protected from external influences such as oxidation or the action exerted by the humidity of the surrounding environment. Protected by the impervious outer layer, the volatile constituents of the active base will thus be retained inside the packaging until it is opened when they will disperse into the surrounding atmosphere and will exert their perfuming, deodorizing, bactericidal or other type of action.

Alternatively the polymeric sheet of the invention can be used to make packagings whose outer layer would be constituted by the polymeric material containing the active base and whose inner layer would be constituted by the impervious polymeric material. Here, it is a question of when a packaging is desired which is able to give off an odour while guaranteeing impermeability with regard to the product contained in the packaging. Embodiments of the packaging of the material will be described by way of example with reference to the attached drawings, in which.

Figure 1:
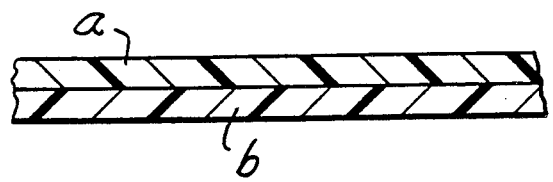
FIG. 1 represents a lateral cross-section of a two-layered sandwich sheet.
Figure 2:
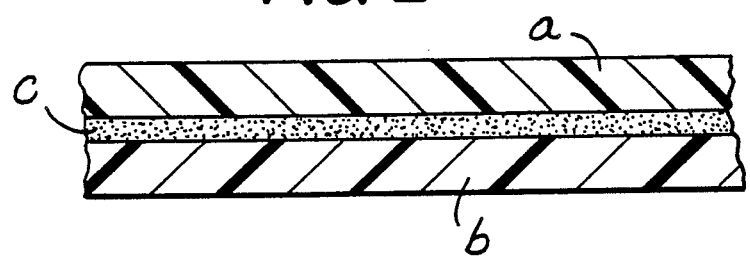
FIG. 2 represents a lateral cross-section of a two-layered sandwich sheet, the layers stuck together by gluing.

The polymeric sandwich sheet represented in FIG. 1 is composed of a layer (a) impervious to the volatile agents of an active base, this layer being stuck to a layer (b) made from a polyolefin-based polymer and containing the active base. FIG. 2 represents a particular embodiment of the sheet according to the invention. The impervious layer (a) is stuck to the pervious layer (b) by gluing, with the help of an adhesive substance (c).

Figure 3:
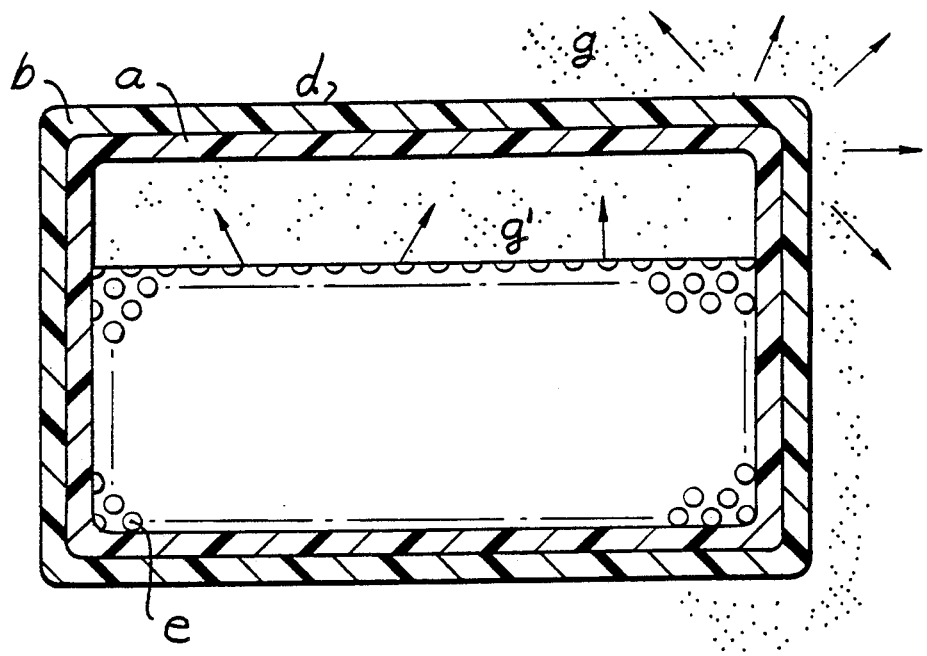
FIG. 3 represents a lateral cross-section of a packaging realized with the help of a two-layered sandwich sheet according to the invention and containing a scented product in granular form.

FIG. 3 represents a packaging (d) made with the help of the sheet according to the invention. The packaging comprises walls constituted by a two-layered sheet, whose inner layer (a) is impermeable to the volatile vapors (g') being given off from the granular, scented product (e) contained in the packaging, while the outer layer (d) is made from a polyolefin-based polymer and serves as a medium for an active base able to give off sanitizing vapours (g) into the surrounding atmosphere.

Figure 4:
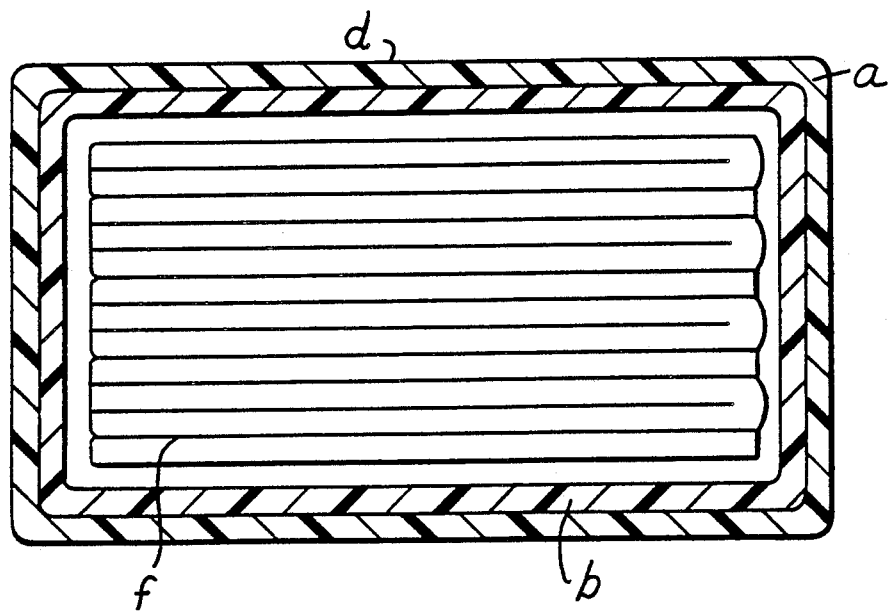
FIG. 4 represents a lateral cross-section of a packaging whose walls are constituted by a two-layered sandwich sheet according to the invention and containing paper handkerchiefs.

FIG. 4 represents a packaging (d) made with the help of the sheet according to the invention and containing paper handkerchiefs or tissues (f). The packaging comprises walls constituted by a two-layered sheet, whose inner layer (b) serves as a medium for an active base able to give off scented and/or bactericidal vapours into the interior of the packaging, while the outer layer (a) is impervious to the said vapors.

Figure 5:
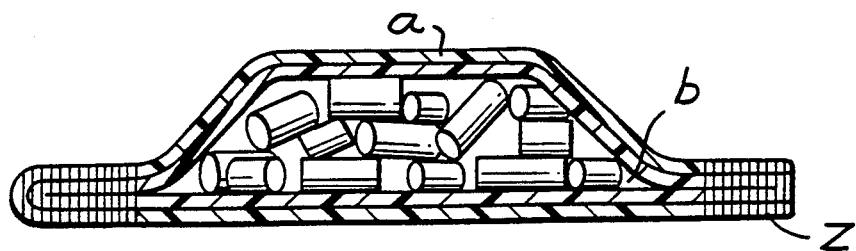
FIG. 5 represents a lateral cross-section of a packaging whose walls are constituted by a two-layered sandwich sheet according to the invention and containing a product in granular form.

The packaging represented in FIG. 5 is composed of a compartment containing a product in granular form, the cavity being sealed by the welding (zone z) of a polymeric sandwich sheet according to the invention, constituted by two adhering layers: one layer (a) impermeable to the vapors of an active base and the other layer (b) made from a polyolefin polymer acting as a homogeneous medium for the active base.

Figure 6:
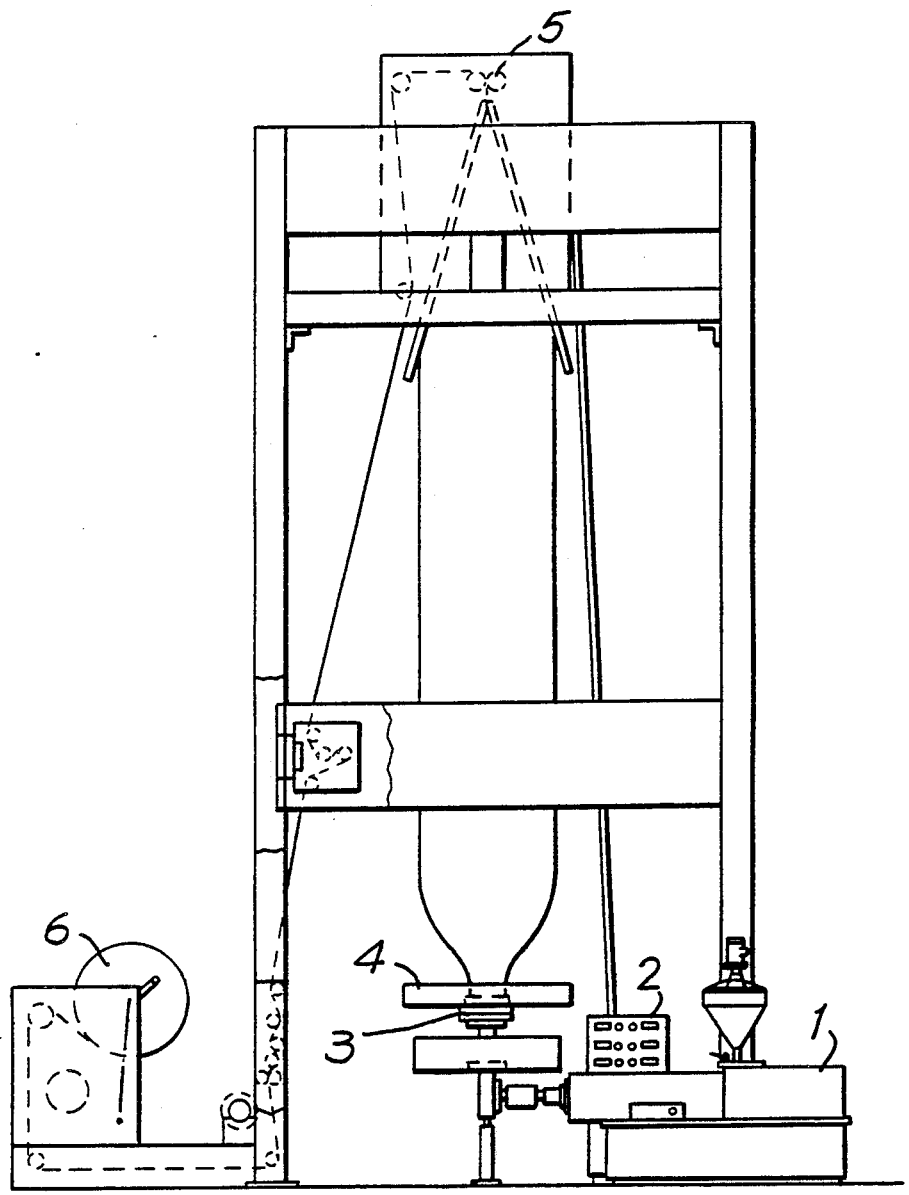
FIG. 6 represents, in the form of a diagram, an apparatus for blown extrusion.

FIG. 6 represents a diagram of apparatus for blown extrusion, used for the preparation of the polymeric sandwich sheet in accordance with the invention. The unit is composed of an extruder 1, a control panel 2, a blowing head 3, a cooling ring 4, a roller 5 for removing the sheets and a system for rolling up the sheets 6.

According to a particular embodiment, the apparatus for blown extrusion is composed of a series of extruders, each one of which permits the extrusion of a separate polymeric material. Each of the melted materials is conveyed to a separate blowing head and arranged concentrically in such a way that, after blowing, the outer roll is constituted by the impermeable polymeric material and the inner roll is constituted by the polymeric materials serving as a diffusion medium for the perfuming, insecticidal or other type of base.

When it is desired to make a sheet constituted by two superimposed and glued layers, one can proceed with the help of a system operating with three extruders, two of which serve to carry out the extrusion of the chosen polymeric resins and the third to carry out the extrusion of the adhesive product. For this purpose one can use ordinary polymeric materials provided for in the art. Elvax (registered trade mark of Du Pont de Nemours), a resin with a base of copolymer of ethylene and vinyl acetate, can be used for this purpose.

The manufacture of the sandwich sheet according to the invention can therefore be easily carried out by means of the blown extrusion technique described above.

However, the other methods of manufacturing sheets are also suitable for use. Thus two or three-layered sheets according to the invention can be manufactured by extrusion coating. This method is particularly suited to the manufacture of sheets whose impervious layer is constituted by a sheet of aluminum for example.

According to the conventional techniques, such a sheet of aluminum can then be covered with paper, if applicable, and the sheet thus obtained can constitute a material suited to the manufacture of standard packagings, particularly for foodstuffs and drinks. By using an aromatized polymeric sheet as an inner layer, one can thus give the contents of the packaging the desired aroma.

The invention is illustrated in more detail by the following examples in which the temperatures are given in degrees centigrade.

EXAMPLE 1

A. Manufacture of a sheet by blown extrusion

A polymeric sandwich sheet with a base of polyethylene and polyamide was prepared by means of an apparatus for blown extrusion, this apparatus equipped with three extruders arranged in a star formation, their outlets being brought together in a blowing head with three nozzles (pilot equipment of the Du Pont de Nemours Company, Geneva).

The three extruders have been fed separately with a. polyamide (Durethan C38F; Bayer AG),
b. adhesive E148 (Du Pont de Nemours), and
c. polyethylene (Baylon 1555F14; Bayer AG).

Some granulated polyethylene was mixed beforehand with a perfuming or aromatising base in the proportion of 20 parts of base to 80 parts of polyethylene. After mixing, this mixture was left to stand at atmospheric temperature for 24 hours, so that the liquid base is totally absorbed into the polymeric medium. This mixture was then added before extrusion to the granulated polyethylene mass, in a proportion of 2.5 g of scented mixture to 97.5 g of polyethylene.

The polymeric resins a, b, c were extruded so as to constitute the outer, median and inner layers respectively of the issuing film. The extrusion temperature was 210°C. The cooling of the issuing film was carried out with the help of a current of air. The film obtained was rolled up in tube form without being cut and used straightaway for the manufacture of packaging as described below in the example given. The three layers had a thickness of 20, 10 and 25 microns respectively for the outer, intermediate and inner layers.

B. Manufacture of a sheet by extrusion coating

A pilot apparatus from the company Du Pont de Nemours, equipped with three extruders arranged in parallel, each having a flat nozzle for the extrusion of a thin film of 50 cm in width, was used for manufacturing of this type. First of all there was manufactured a two-layered sheet, one layer of which was constituted by an aluminum film, 12 microns thick, and the other of which was constituted by white paper of the 50 g/m² variety, the two layers being stuck with the help of a standard adhesive.

Separately there was prepared a concentrated granulate consituted by a copolymer of polyethylene vinyl acetate [Elvax (registered trade mark) 150; Du Pont de Nemours] perfumed or aromatized with a suitable base and selected according to the product whose packaging is desired (see following examples). The proportion of the base in relation to the polymeric granulate was 20 parts of base to 80 parts of polymeric resin.

Before extrusion, the perfumed granulate thus obtained was mixed with the mass of Surlyn [(registered trade mark) 1652; Du Pont de Nemours] at a concentration of 2.5% and the resulting resin was extruded by being coated onto the previously obtained aluminum layer (see above) so as to obtain a film 30 microns thick. The extrusion temperature was 235°.

The resulting film was cooled immediately on a cold roller at the outlet of the extruder and rolled up.

EXAMPLE 2

Perfuming of a packaging for paper handkerchiefs

A polymeric sandwich sheet prepared in accordance with the process described in Example 1A and constituted by a polyamide impervious layer of 20 microns and a polyethylene layer of 20 microns, the latter having been scented in the proportion of 0.5% by weight with the help of a composition of the mint type (Peppermint Naefco; origin: Firmenich SA) or cypress type (Cypress 41.463; origin: Firmenich SA), was used to package paper handkerchiefs of standard quality, Tela (registered trade mark).

The packaging was made by welding the edges of the sheet by means of an impulse welding machine.

In such a packaging, after only a few days, the handkerchiefs acquire a distinct scent, characteristic of the composition used. Such a scent is pleasantly given off into the surrounding atmosphere when the packaging is opened.

EXAMPLE 3

Scenting of a packaging for artificial flowers made of paper or silk

A packaging was prepared, intended for artificial flowers made of paper or silk, using a sheet obtained in accordance with Example 1A, of which one layer was scented with a composition of the carnation variety (Carnation 660.895/B; origin: Firmenich SA) in the proportion of 0.5% by weight.

In a packaging of this type, the flowers had absorbed a part of the volatile vapours of the perfuming composition and gave off a pleasant scent once removed from their packaging.

EXAMPLE 4

Perfuming of a packaging for linen and clothes

In the way indicated in example 1A, a packaging was prepared which was intended to contain linen, by using as the active perfuming composition, a cypress base (Cypress 41.463; origin: Firmenich SA) and a carnation base (Carnation 660.895/B; origin: Firmenich SA). The linen thus packaged acquires a pleasant odour which is given off when the packaging is opened, even after a very lengthy period of time (10 months).

By replacing the perfuming composition with a volatile insecticidal agent [Vaporthrin (registered trade mark); origin: Sumitomo, Osaka, Japan], or a common mothproofing agent (naphtalene), a packaging was obtained whose protective action with regard to external agents has shown itself to be particularly effective. Of course, sheets can also be obtained which possess both a perfuming and an insecticidal action. With the help of the sheet thus obtained, one can therefore manufacture covers intended to contain and satisfactorily protect clothes during a lengthy period of time.

EXAMPLE 5

Perfuming of a packaging for cigarettes

A packaging for cigarettes was prepared using a sheet obtained as indicated in Example 1A. The sheet was perfumed in one of its layers (inner) with the help of a composition of the chocolate variety (Chocolate 660.402/B; origin: Firmenich SA) in the proportion of 0.4% by weight. When the packaging was opened, the emission of volatile vapours could be observed, these pleasantly perfuming the surrounding atmosphere.

A totally similar effect has been observed using a composition of the mentholated variety (Mint Naefco; origin: Firmenich SA) in the proportion of 0.5% by weight.

EXAMPLE 6

Aromatization of a packaging for extruded snacks

A packaging for neutral-tasting extruded maize snacks was prepared with the help of a sheet obtained as indicated in Example 1A and aromatized by means of a composition of the strawberry variety (Strawberry 660.478; origin: Firmenich SA) in the proportion of 0.5% by weight. After only a few days, the snacks had acquired a marked strawberry taste. After 10 months of storage in a sealed packagind, the taste was still pronounced and had not deteriorated.

EXAMPLE 7

Aromatization of a packaging for chocolates, sweets and biscuits

Samples of commercially-available chocolate (pralined), sweets and biscuits were removed from their original packaging and repacked in sheets obtained in accordance with the process described in Example 1A. Indicated below are the compositions used for their aromatization and the effects observed when they were tasted after having been stored for 10 months in the aromatized packaging.

| | | | |
|---|---|---|---|
| 1. | Milk chocolate (Frey Sprot Mocca Nuss) | Chocolate 660.403 (0.3%) | more marked chocolate taste |
| 2 | Mocca milk chocolate Frey) | Coffee 660.447 (0.3%) | more marked odour of coffee |
| 3. | Caramel (Prima Mocca Migros) | Coffee 660.447 (0.3%) | more marked odour, more marked taste |
| 4. | Hollow wafers (Mocca Migros) | Coffee 660.447 (0.3%) | more intense taste |
| 5 | Chocolate dragees (Frey) | Chocolate 660.403 (0.3%) | very big difference in odour, more marked taste |

The effects have been observed by comparison with the original samples. The aromatizing compositions used originate from Firmenich SA; Geneva

EXAMPLE 8

We proceed to prepare a packaging in the form of a rectangular carton intended to contain orange juice, with the help of a sandwich sheet obtained as described in example 1B, whose polyolefin layer had been aromatized with an orange base (Orange 51.941/A; origin: Firmenich SA) in the proportion of 0.4%. Some commercially-available orange juice (Migros-naturel quality) was packaged in the rectangular carton obtained and stored for a month in a refrigerator, then compared with a sample of orange juice of identical quality packaged in a packaging constituted by a laminated paper-aluminum-Surlyn sheet.

The organoleptic evaluation carried out by 12 experts has shown that the drink packaged in the sandwich sheet according to the invention had a fresher, more aromatic note.

EXAMPLE 9

A commercially-available apple juice (origin: Migros-limpide) was packaged in a manner identical to that described in Example 8 and the drink was stored in a refrigerator for one month, then compared with a sample of commercially-available apple juice. The polyolefin layer of the sandwich sheet had been aromatized with an apple aroma (Apple 52.681/T; origin: Firmenich SA) in the proportion of 0.4%.

The members of the panel who were called to five a verdict on the organoleptic qualities of the two products have found that the drink packaged in the sandwich sheet according to the invention had a fresher and more aromatic note and was less sickly sweet than the original drink.

What I claim is:

1. A multilayer sandwich sheeting comprising at least two separately and simultaneously extruded layers of polymeric materials, a first layer being composed of a first polymeric material selected from a group consisting of a polyolefin resin and a copolymer of polyamide and polyether, said first polymeric material being mixed before extruding with a volatile active agent selected from the group consisting of a perfuming composition, a deodorizing composition, a flavoring agent, an aroma agent, an insecticidal substance and a bactericidal substance; and a second layer being composed of a second polymeric material which is impervious to said volatile active agent, said second layer being extruded as the outer layer while the first layer forms the inner layer, such that evaporation of said volatile active agent is substantially prevented during said extrusion; said first and second layers being permanently stuck together.

2. Packaging formed from a multilayer sandwich sheeting comprising at least two separately and simultaneously extruded layers of polymeric materials, a first layer being composed of a first polymeric material selected from a group consisting of a polyolefin resin and a copolymer of polyamide and polyether, said first polymeric material being mixed before extruding with a volatile active agent selected from the group consisting of a perfuming composition, a deodorizing composition, a flavoring agent, an aroma agent, an insecticidal substance and a bactericidal substance; and a second layer being composed of a second polymeric material which is impervious to said volatile active agent, said second layer being extruded as the outer layer while the first layer forms the inner layer, such that evaporation of said volatile active agent is substantially prevented during said extrusion; said first and second layers being permanently stuck together.

3. Packaging formed from the sandwich sheet of claim 2, wherein the second layer forms the outside of the package.

4. A multilayer sandwich sheeting which is prepared by separately and simultaneously co-extruding in a current of air or inert gas at least two layers which are superimposed and permanently bound together, one of said layers being composed of a material impervious to a volatile active agent and the other said layer being composed of a film made from a polymeric material, said film being 10 to 300 microns thick and containing said active agent premixed in a homogenous manner in said polymeric material prior to extrusion in a proportion of 0.1 to 50% active agent by weight to the weight of said polymeric material in which said active agent is incorporated, the said impervious layer being extruded as the outer layer while the said active agent containing layer forms the inner layer such that evaporation of said active agent is prevented during simultaneous co-extrusion of said layers.

5. The sandwich sheet according to claim 4, wherein the film comprises a polyolefin resin.

6. The sandwich sheet according to claim 5, wherein the polyolefin resin comprises polyethylene, polypropylene, or copolymers of ethylene and propylene, ethylene and vinyl acetate, or ethylene and ethyl acrylate.

7. The sandwich sheet according to claim 4, wherein the film comprises a copolymer of polyamide and polyether.

8. The sandwich sheet according to claim 4, wherein the layer impervious to the volatile active agents comprises one of aluminum or a polyamide or polyester resin.

9. The sandwich sheet according to claim 4, wherein the two layers are superimposed and permanently bound together by gluing with an adhesive substance.

10. The sandwich sheet according to claim 9, wherein the adhesive substance is premixed with one of a perfuming composition, a deodorizing composition, an aroma agent, an insecticidal substance, or a bactericidal substance.

11. A multilayer sandwich sheeting which is prepared by separately and simultaneously co-extruding in a current of air or inert gas at least two layers which are superimposed and permanently bound together, one of said layers being composed of a material impervious to a volatile active agent and the other said layer being composed of a film made from a polymeric material, said film being 10 to 300 microns thick and containing said active agent premixed in a homogeneous manner in said polymeric material prior to extrusion in a proportion of 0.1 to 50% active agent by weight to the weight of said polymeric material in which said active agent is incorporated, said volatile active agent being selected from the group consisting of a perfuming composition, a deodorizing composition, a flavoring agent, an aroma agent, an insecticidal substance and a bactericidal substance, the said impervious layer being extruded as the outer layer while the said active agent containing layer forms the inner layer such that evaporation of said active agent is prevented during simultaneous co-extrusion of said layers.

12. Packaging formed from a multilayer sandwich sheeting which is prepared by separately and simultaneously co-extruding in a current of air or inert gas at least two layers which are superimposed and permanently bound together, one of said layers consisting of a material impervious to a volatile active agent and the other said layer being composed of a film made from a polymeric material, said film being 10 to 300 microns thick and containing said active agent premixed in a homogenous manner in said polymeric material prior to extrusion in a proportion of 0.1 to 50% active agent by weight to the weight of said polymeric material in which said active agent is incorporated, the said impervious layer being extruded as the exterior layer while the said active agent containing layer forms the interior layer such that evaporation of said active agent is prevented during simultaneous co-extrusion of said layers.

13. The packaging according to claim 12, wherein the film comprises a polyolefin resin.

14. The packaging according to claim 13, wherein the polyolefin resin comprises polyethylene, polypropylene, or copolymers of ethylene and propylene, ethylene and vinyl acetate, or ethylene and ethyl acrylate.

15. The packaging according to claim 12, wherein the film comprises a copolymer of polyamide and polyether.

16. The packaging according to claim 12, wherein the layer impervious to the volatile active agents comprises aluminum or a polyamide or polyester resin.

17. The packaging according to claim 12, wherein the two layers are superimposed and permanently bound together by gluing with an adhesive substance.

18. The packaging according to claim 17, wherein the adhesive substance is premixed with one of a perfuming composition, a deodorizing composition, an aroma agent, an insecticidal substance, or a bactericidal substance.

19. Packaging formed from a multilayer sandwich sheeting which is prepared by separately and simultaneously coextruding in a current of air or inert gas at least two layers which are superimposed and permanently bound together, one of said layers consisting of a material impervious to a volatile active agent and the other said layer being composed of a film made from a polymeric material, said film being 10 to 300 microns thick and containing said active agent premixed in a homogeneous manner in said polymeric material prior to extrusion in a proportion of 0.1 to 50% active agent by weight to the weight of said polymeric material in which said active agent is incorporated, said volatile active agent being selected from the group consisting of a perfuming composition, a deodorizing composition, a flavoring agent, an aroma agent, an insecticidal substance, and a bactericidal substance, the said impervious layer being extruded as the exterior layer while the said active agent containing layer forms the interior layer such that the evaporation of said active agent is prevented during simultaneous co-extrusion of said layers.

20. A multilayer sandwich sheeting which is prepared by separately and simultaneously co-extruding in a current of air or inert gas at least two layers which are superimposed and permanently bound together, one of said layers being composed of a material impervious to a volatile active agent and the other said layer being composed of a film made from a polymeric material, said film being 10 to 300 microns thick and containing said active agent premixed in a homogeneous manner in said polymeric material prior to extrusion in a proportion of 0.1 to 50% active agent by weight to the weight of said polymeric material in which said active agent is incorporated, said volatile active agent being selected from among compounds having sanitizing or aromatizing characteristics, the said impervious layer being extruded as the outer layer while the said active agent containing layer forms the inner layer such that evaporation of said active agent is prevented during simultaneous co-extrusion of said layers.

* * * * *